United States Patent [19]
Arendsen et al.

[11] 3,947,462
[45] Mar. 30, 1976

[54] 2,4,7-SUBSTITUTED 5-HYDROXY BENZOPYRANS AND ESTERS

[75] Inventors: David Lloyd Arendsen, Libertyville; Martin Winn, Deerfield, both of Ill.

[73] Assignee: Abbott Laboratories, North Chicago, Ill.

[22] Filed: May 22, 1974

[21] Appl. No.: 472,243

[52] U.S. Cl. 260/295 F; 260/247.2 A; 260/293.5 S; 260/297 B; 424/246; 424/248; 424/263
[51] Int. Cl.² ................................. C07D 311/60
[58] Field of Search ................. 260/295 F, 297 B

[56] References Cited
UNITED STATES PATENTS

| | | | |
|---|---|---|---|
| 3,707,474 | 12/1972 | Razdan et al. | 260/295 F |
| 3,726,883 | 4/1973 | Razdan et al. | 260/295 F |
| 3,804,841 | 4/1974 | Razdan et al. | 260/295 F |
| 3,853,899 | 12/1974 | Fake | 260/295 F |

*Primary Examiner*—Norman A. Drezin
*Attorney, Agent, or Firm*—Robert L. Niblack; Vincent A. Mallare

[57] ABSTRACT

2,4,7-Substituted 5-hydroxy benzopyrans and dihydrobenzopyrans and their esters represented by the formulae

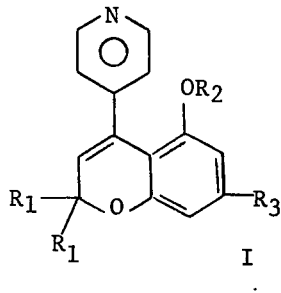

or

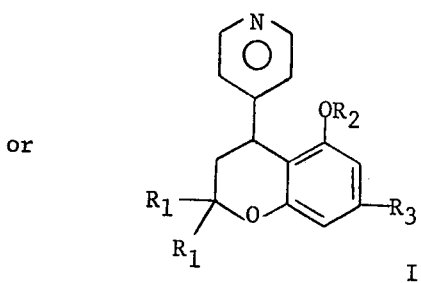

wherein each $R_1$ is loweralkyl, and $R_2$ is hydrogen, loweralkanoyl or

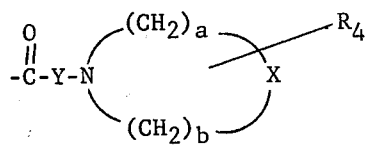

with Y being a straight or branched chain alkylene group having from 1–8 carbon atoms; a is an integer from 1–4; b is an integer from 1–4; X is $CH_2$, O, S, or $NR_5$ with $R_5$ being hydrogen or loweralkyl, with the limitation that when X is O, S, or $NR_5$, the sum of a and b is 3 or 4 and $R_4$ is hydrogen or loweralkyl; and $R_3$ is

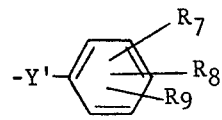

with Y' being a straight or branched chain alkylene group having from 1–10 carbon atoms; and each $R_7$, $R_8$ and $R_9$ are the same or different members of the group consisting of hydrogen, halo, trifluoromethyl or loweralkyl and the pharmaceutically acceptable salts thereof.

5 Claims, No Drawings

2,4,7-SUBSTITUTED 5-HYDROXY BENZOPYRANS AND ESTERS

DETAILED DESCRIPTION OF THE INVENTION

This invention relates to novel 2,4,7-substituted 5-hydroxy benzopyrans and esters and to pharmaceutical compositions containing the compounds for pharmacological and medicinal purposes.

According to one aspect of the invention, compounds are provided which can be represented by the formula

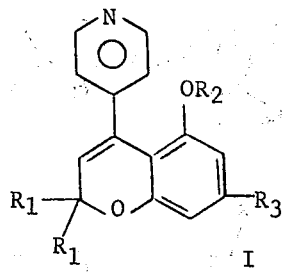

I or

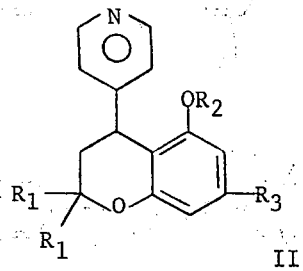

II wherein each $R_1$ is loweralkyl, and $R_2$ is hydrogen, lower-alkanoyl or

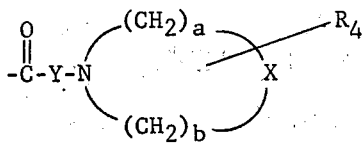

with Y being a straight or branched chain alkylene group having from 1–8 carbon atoms; $a$ is an integer from 1–4; $b$ is an integer from 1–4; X is $CH_2$, O, S, or $NR_5$ with $R_5$ being hydrogen or loweralkyl, with the limitation that when X is O, S, or $NR_5$, the sum of $a$ and $b$ is 3 or 4 and $R_4$ is hydrogen or loweralkyl; and $R_3$ is

with Y' being a straight or branched chain alkylene group having from 1–10 carbon atoms; and each $R_7$, $R_8$ and $R_9$ are the same or different members of the group consisting of hydrogen, halo, trifluoromethyl or loweralkyl and the pharmaceutically acceptable salts thereof.

The term "loweralkyl" as used herein, refers to $C_1$–$C_6$ straight or branched chain alkyl groups containing methyl, ethyl, n-propyl, iso-propyl, n-butyl, sec-butyl, tert-butyl, n-pentyl, iso-pentyl, neo-pentyl, n-hexyl and the like.

The term "loweralkanoyl" as used herein, refers to saturated monovalent, aliphatic radicals derived from a monocarboxylic acid, including straight or branched chain radicals of from 1–6 carbon atoms including the formyl, acetyl, propionyl, α-methylpropionyl, butyryl, hexanoyl and the like radicals.

The term "pharmaceutically acceptable salts" refers to those such as sodium, potassium, calcium, barium, aluminum, ammonium and substituted ammonium salts, such as methyl ammonium, benzyl ammonium, triethanol ammonium salts and the like. The term includes both cationic salts which are well known in the art and are considered "pharmaceutically acceptable".

The term "pharmaceutically acceptable acid addition salts" refers to acid addition salts which are those salts prepared for example, by reacting the basic esters with an organic or inorganic acid, or by reacting the benzopyrans with an acid addition salt of the desired acid. Representative salts include the hydrochloride, hydrobromide, sulfate, bisulfate, acetate, valerate, oleate, laurate, borate, benzoate, lactate, phosphate, tosylate, citrate, maleate, succinate, tartrate and the like.

Intermediate pyrones useful in making the compounds of Formulae I and II are represented by Formulae III and IV:

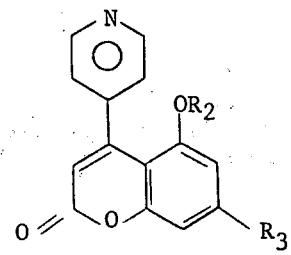

III or

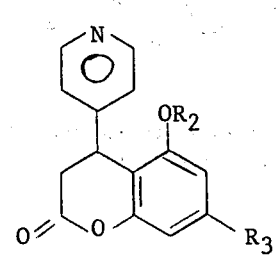

IV

In producing the intermediate resorcinols, an appropriate arylalkyl halide is converted to a Grignard reagent and then reacted with 3,5-dimethoxy acetophenone (or higher homolog). The resulting alcohol is hydrogenated and then the methoxy groups are converted into hydroxy groups with HBr.

Alternatively, the arylalkyl halide is reacted with 3,5-dimethoxy propiophenone (or higher homolog) in the presence of sodium hydride (or other appropriate base) and the resulting ketone is treated with an alkyl magnesium halide. The resulting alcohol is hydrogenated and converted into the resorcinol with HBr.

The substituted resorcinol is reacted with a keto ester containing the desired $R_1$ group to form a coumarin.

The coumarin is then reacted with $CH_3MgBr$ to give the benzopyran, which can be hydrogenated to the dihydro benzopyran.

Alternatively, the resorcinol can be reacted with methyl crotonic acid according to the method of Fahrenholtz [J. Am. Chem. Soc. 89 5934 (1967)] to give the benzopyran-4-one which in turn is reacted with a Grignard or other organometallic compound to give the desired benzopyran.

The benzopyran or dihydro benzopyran is then esterified with either an acid or acid chloride containing the $R_2$ group to form the final product.

Instead of proceeding from the pyrone to the pyran to achieve the dihydropyran one may reduce the pyrone to the dihydropyrone, and then effect a Grignard reaction to prepare the dihydropyran.

The following flow diagrams illustrate these methods of preparation:

a) Preparation of the 5-Substituted Resorcinol:

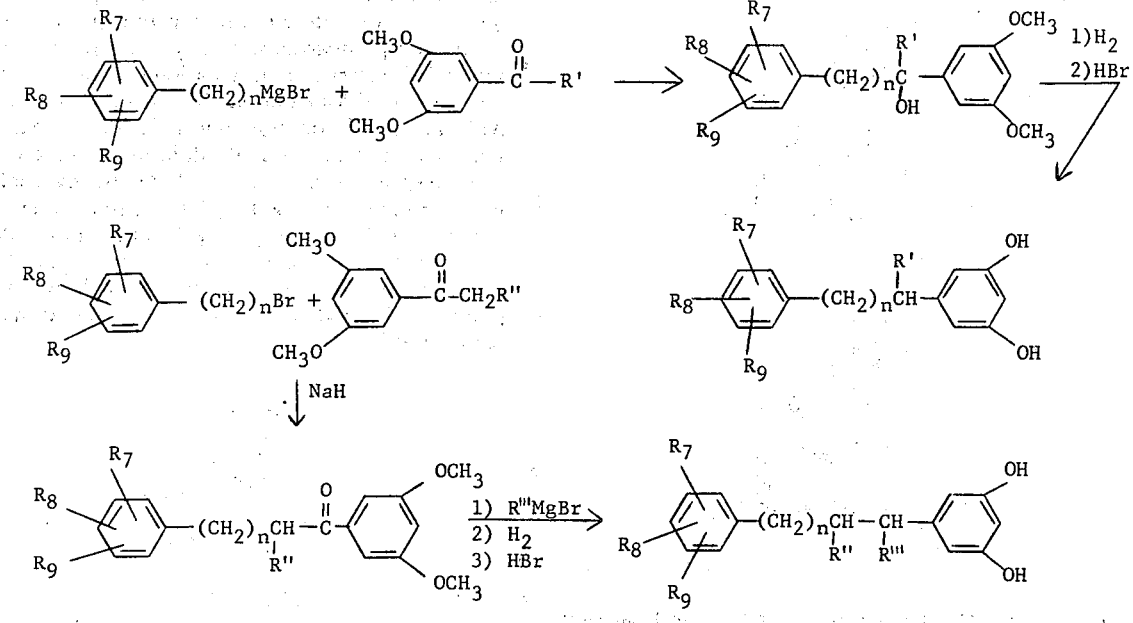

b) Preparation of the Benzopyran:

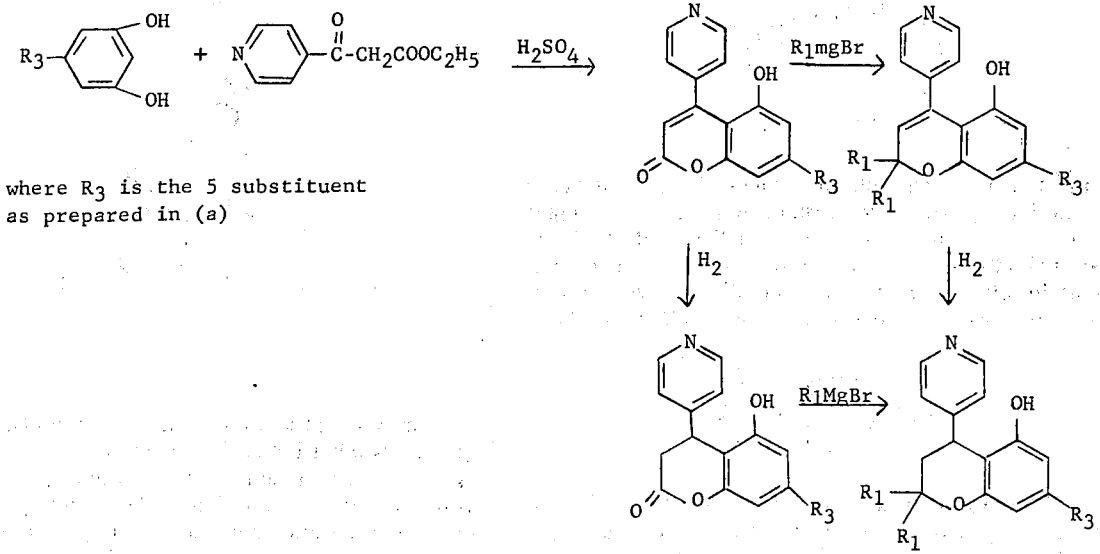

where $R_3$ is the 5 substituent as prepared in (a)

b) Continued

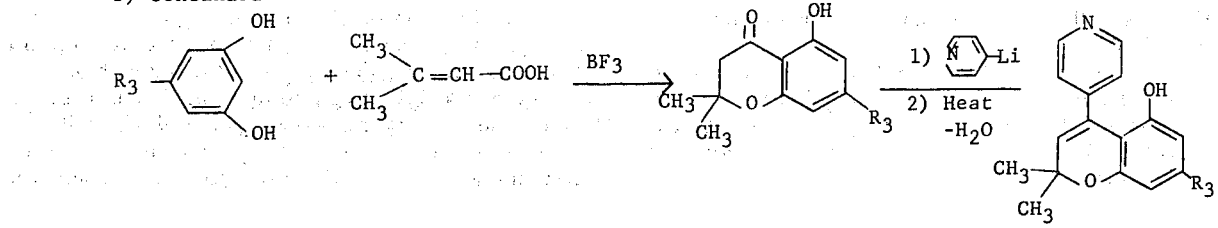

c) Preparation of the Ester:

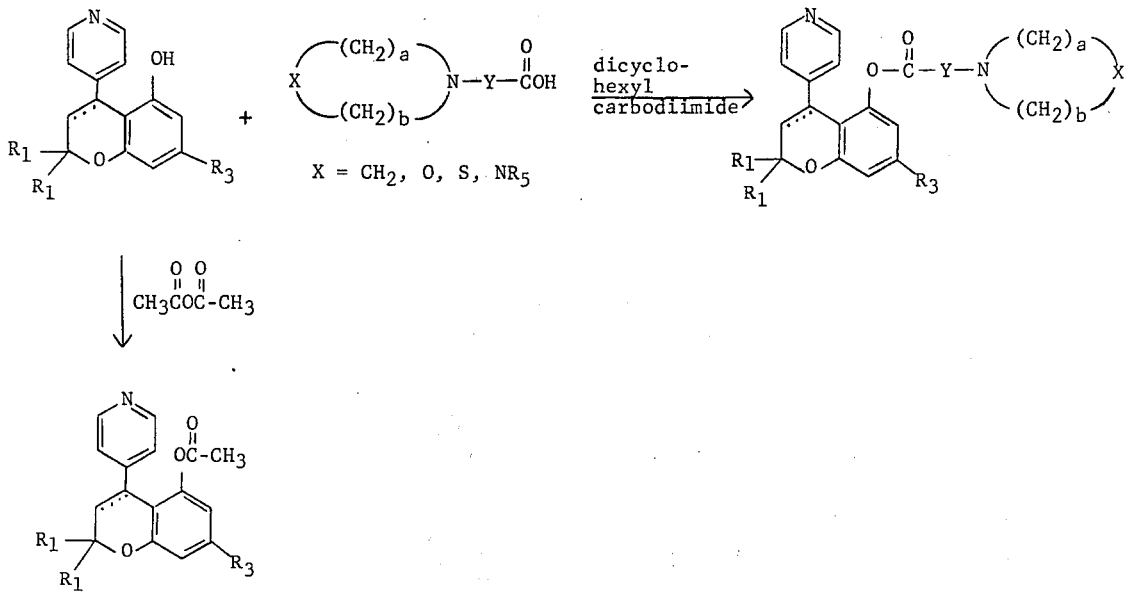

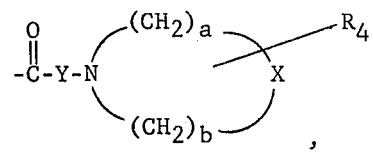

Compounds of Formula I are useful as analgesic agents when administered to an animal either orally or parenterally at dosages of from 0.4 to 40 mg./kg. of body weight daily, preferably in divided dosages of from 2 to 4 times daily. The analgesic activity was first established in the mouse writhing test by the method of B. A. Whittle (Brit. J. Pharmacol., 1964, 22:246) and is modified by eliminating the intravenous dye injection and assay; and reducing the pre-treatment time to one hour prior to acid injection, using groups of five mice.

The presently preferred compounds of Formula I are those wherein each $R_1$ is methyl, $R_2$ is H or $COCH_3$ and $R_4$ is 4-fluorophenyl-2-pentyl. The presently preferred compounds have $ED_{50}$'s of 4.1 and 10.3 respectively.

In addition to their analgesic activity, the compounds of Formula I are mild tranquilizing agents at dosages of from 0.5 to 50 mg./kg. of body weight daily by oral or parenteral administration. The tranquilizing activity was first established in the mouse fighting test by the method of Tedeshi et al., [J. Pharmacol. Exp. Ther. 125 28 (1959)]. Since pain is generally accompanied by anxiety, the compounds of this invention are especially useful for treating patients suffering from pain.

Some of the compounds of Formula I, for example, when each $R_1$ is methyl, $R_2$ is $COCH_3$ and $R_4$ is 4-fluorophenyl-2-pentyl, additionally exhibit antidepressant activity at dosages of from 0.5 to 200 mg./kg. of body weight daily and these are useful as anti-anxiety agents because of the combination of their tranquilizing effect without stimulating overtones. The antidepressant activity was first established in the modified dopa test, according to the method of G. M. Everett, Antidepressant Drugs, Proc. Int. Symp. 1, 194 (1967).

The compounds of Formula II are useful as antidepressant agents at oral and parenteral dosages of from 0.5 to 200 mg./kg. of body weight daily. The antidepressant activity was first established in the modified dopa test and confirmed in the reserpine reversal test according to the method of R. Domenjoz and W. Theobold, Arch. Int. Pharmacodyn 120 458 (1959).

Compounds of Formulae III and IV are intermediates useful in the preparation of the compounds of Formulae I and II.

Compounds of Formulae I and II wherein $R_2$ is $$-\overset{O}{\underset{\|}{C}}-Y-N\underset{(CH_2)_b}{\overset{(CH_2)_a}{\diagdown}}X-R_4,$$

the heterocyclic esters, have the advantage of increasing solubility and therefore, lend themselves to ease of administration.

The following examples further illustrate this invention without, however, limiting it thereto.

EXAMPLE 1

Preparation of 2-(3,5-Dimethoxyphenyl)-5-(4-Fluorophenyl)Pentane

A solution of 77 g. of 3-(4-fluorophenyl)propylbromide in 300 ml. of ether was added dropwise over a two hour period to a refluxing solution of 10 g. of magnesium in 100 ml. of ether. The reaction mixture was refluxed for an additional 30 minutes after the addition was completed. A solution of 68 g. of 3,5-dimethoxyacetophenone in 100 ml. of ether was then added dropwise to the reaction and the reaction mixture was refluxed for 1½ hours. To the reaction was added 300 ml. of a saturated ammonium chloride solution dropwise with stirring. The layers were separated and the aqueous layer extracted with ether. The ether extract was dried over magnesium sulfate and the ether removed in vacuo to give an oil. An additional 111.7 g. of 3(4-fluorophenyl)propylbromide was reacted with 3,5-dimethoxyacetophenone in the above manner. The products from both runs were hydrogenated in ethanol-HCl using palladium as the catalyst. The solvents and catalyst were removed and the crude material distilled to yield 169.0 g. of 2-(3,5-dimethoxyphenyl)-5-(4-fluorophenyl)pentane, b.p. 145-155/0.05 mm Hg.

Analysis Calcd. for $C_{19}H_{23}O_2F$: C, 75.60; H, 7.69. Found: C, 75.87; H, 7.98.

EXAMPLE 2

5-Hydroxy-7-[5-(4-Fluorophenyl)-2-Pentyl]-4-(4-Pyridyl)Coumarin 20 g. of the dimethyl ether of Example 1 was reacted with 200 ml. of acetic acid, 80 ml. of 48% hydrobromic acid and 32 g. of dry hydrogen bromide gas at 85° for 16 hours to prepare the resorcinol (Compound B). Compound B was then reacted with 15.25 g. (0.079 mole) of ethyl isonicotinoyl acetate, in the presence of 27 g. of $POCl_3$ and 41 ml. of $H_2SO_4$. The ester was added to the resorcinol and cooling effected by means of an ice bath. The reaction was stirred for approximately 64 hours and allowed, during this time, to warm up to room temperature. Water and chloroform were then added to the reaction mass, the chloroform layer separated and washed with water, and then neutralized with potassium bicarbonate solution. The chloroform layer was then dried over magnesium sulfate, filtered and evaporated to obtain an oil. The oil was crystallized from ethyl acetate, and then recrystallized from ethyl acetate to obtain a product having a m.p. of 205°–206°C. NMR confirmed the structure.

EXAMPLE 3

2,2-Dimethyl-5-Hydroxy-7-[5-(4-Fluorophenyl)-2-Pentyl]-4-(4-Pyridyl)-2H-1-Benzopyran 9.28 g. (0.023 mole) of the coumarin (compound A) of Example 2 was suspended in 40 ml. of dry benzene. Ninety ml. (0.27 mole) of methylmagnesium bromide (3 molar) in 75 ml. of dry ether were placed in a flask under a nitrogen atmosphere. Compound A was then added to the Grignard-ether solution over a period of 15 minutes. Thereafter, the reaction mixture was allowed to stir at room temperature for sixteen hours. The Grignard reaction was then decomposed over 1¾ hours with a saturated ammoniium chloride solution to obtain two layers. The ether layer was separated, dried over magnesium sulfate and evaporated. Thereafter, the product was taken up in 70 ml. of acetic acid. After heating under reflux for two hours, the product was cooled and neutralized with sodium bicarbonate after stripping off the acetic acid. Ethyl ether was then used to extract the organic layer, the ether extract washed and then evaporated. The product crystallized from the ether solution and after recrystallization has a m.p. of 174°–175°C. After drying in a vacuum oven for two days, the product had a m.p. of 168°–169°C. NMR confirmed the desired product structure.

Analysis Calcd. for $C_{27}H_{28}FNO_2$: C, 77.67; H, 6.76; N, 3.35. Found: C, 77.69; H, 6.93; N, 326.

EXAMPLE 4

3,4-Dihydro-2,2-Dimethyl-5-Hydroxy-7-[5-(4-Fluorophenyl)-2-Pentyl]-4-(4-Pyridyl)-2H-1-Benzopyran 3.0 g. (0.0072 mole) of the compound of Example 3 was hydrogenated in 100 ml. of ethanol at 3 atmospheres employing 0.7 g. of 5% Pd/C. After the reaction was completed the ethanol was stripped off, the obtained white glass dissolved in ether and a white solid isolated which, after recrystallization from acetonitrile, gave a m.p. of 162°–164°C. The structure was confirmed by NMR.

Analysis Calcd. for $C_{27}H_{30}FNO_2$: C, 77.30; H, 7.21; N, 3.34 Found: C, 77.56; H, 7.28; N, 3.37.

EXAMPLE 5

5-Acetoxy-2,2-Dimethyl-7-[5-(4-Fluorophenyl)-2-Pentyl]-4-(4Pyridyl)-2H-1-Benzopyran 4.17 g. (0.01 mole) of the hydroxy compound of Example 3 was dissolved in 8 ml. of dry pyridine to which was added 1.22 g. (0.012 mole) of acetic anhydride. The reaction was stirred at room temperature overnight, evaporated, treated with benzene and evaporated again. The residue was taken up in ether, washed with water, dried over magnesium sulfate and evaporated. The compound was then purified on a Florosil activated aluminum magnesium silicate column using methanolbenzene as an eluting solvent to obtain a glass residue. IR and Raman spectra confirmed the structure.

Analysis Calcd. for C, 75.79; H, 6.58; N, 3.05. Found: C, 76.11; H, 6.64; N, 2.84;

EXAMPLE 6

7[5-(4-Fluorophenyl)-2-Pentyl]-2,2-Dimethyl-5-Hydroxy-2,3-Dihydro-4-Oxo-4H-1-Benzopyran 80 g. of 2(3,5-dimethoxyphenyl)-5-(4-fluorophenyl) pentane was converted into the resorcinol by treating with 670 ml. of acetic acid, 270 ml. 48% HBr, 105 g. HBr gas at 85° for 16 hours.

To this resorcinol was added 31.2 g. of 3-methyl crotonic acid and the mixture was heated to 110°C. Then 62 ml. boron fluoride etherate was added and the mixture kept at 120° for 16 hours. The solution was cooled, then treated with 90 ml. water and 350 ml. 6N NaOH and boiled for 5 minutes on a steambath. After cooling and acidifying with 6N HCl, the mixture was extracted with ether. The ether layer was extracted with 3 portions of 1N NaOH, followed by 1 portion of 5% HCl. The ether layer was dried over $MgSO_4$ and concentrated. The product was chromatographed on a Florisil activated aluminum magnesium silicate column eluting with 3% ether and 97% hexane. Yield 46.8 g. of the desired product as a colorless oil; 50% yield.

Analysis Calcd. for $C_{22}H_{25}FO_3$: C, 74.13; H, 7.09. Found: C, 74.16; H, 7.38.

EXAMPLE 7

2,2-Dimethyl-5-Hydroxy-7-[5-(4-Fluoropphenyl)-2-Pentyl]-4-(4-Pyridyl)-2H-Benzo[1]Pyran 13.3 g. 4-bromopyridine is converted to 4-pyridyllithium by reaction with butyl lithium in ether at −45°C. Then 5.00 g. of [5-(4-fluorophenyl)-2-pentyl]-2,2-dimethyl-5-hydroxy 2,3-dihydro-4-oxo-4H-1-benzopyran (Example 6) is added and the solution kept at −15°C. for 20 minutes. The reaction mixture is worked up with sulfuric and water giving the intermediate 4,5-dihydroxy-2,2-dimethyl-7-[5-(4-fluorophenyl)-2-pentyl]-4-(4-pyridyl)chroman, and this is heated in vacuum at 190° for 45 minutes givng the product identical to the product of Example 3.

EXAMPLE 8

5-Hydroxy-7-[5-(4-Fluorophenyl)-2-Pentyl]-4-(4-Pyridyl)-3,4-Dihydro Coumarin

The coumarin of Example 2 (2.2 g) was hydrogenated in ethanol using 5% palladium on carbon as a catalyst. The resulting oil was purified on a Florisil column, eluting with chloroform to give the desired product.

EXAMPLE 9

5[4-(1-Piperidino)Butyryloxy]-2,2-Dimethyl-7-[5-(4-Fluorophenyl)-2-Pentyl]-4-(4-Pyridyl) Chroman The hydroxy compound of Example 4 (2.80 g.) was reacted with 1.39 g. of 4-piperidino butyric acid HCl [Cruickshank and Sheehan, J. Am. Chem. Soc., 83, 2891 (1961)] and 1.48 g. dicyclohexyl carbodiimide (DCC) in 125 ml. dry methylene chloride. After stirring 16 hours, the dicyclohexylurea formed was filtered and the filtrate was concentrated to a gummy residue which was the desired product. Nmr analysis was consistent with the desired structure.

Analysis Calcd. for $C_{36}H_{46}ClFN_2O_3$: C, 70.98; H, 7.61; N, 4.60. Found: C, 70.30; H, 7.75; N, 4.68.

EXAMPLE 10

5-[4-(4-Morpholino)Butyryloxy]-2,2-Dimethyl-7-[5-(4-Fluorophenyl)-2-Pentyl]-4-(4-Pyridyl)Chroman The hydroxy compound of Example 4 (2.80 g.) was reacted with 1.40 g. of 4-morpholino butyric acid [J. Am. Chem. Soc. 83, 2891 (1961)] and 1.48 g. DCC as described above (Example 9). The product was crystallized from $CH_2Cl_2$ ether and had a m.p. of 118°–120°.

Analysis Calcd. for $C_{35}H_{49}ClFN_2O_4$: C, 68.78; H, 7.26; N, 4.58. Found: C, 67.95; H, 7.19; N, 4.73.

EXAMPLE 11

γ-Homopiperidinobutyric Acid Hydrochloride 23.0 g. (0.1 mmole) of methyl-γ-iodoburyrate [F. F. Blicke, W. B. Wright and M. F. Zienty, J. Amer. Chem. Soc., 63, 2488 (1941)] was combined with 25.0 g. (0.4 mole) of homopiperidine (Aldrich) and heated at 70° for three hours. The precipitate of amine hydroiodide was removed by filtration and the filtrate was concentrated to an orange oil. The methyl γ-homopiperidinobutyrate distilled as 14.0 g. of colorless liquid at 0.5 mm., b.p. 70°–71°. This material was dissolved in 75 ml. of aqueous 18% hydrochloric acid solution and heated at reflux for 16 hours. The solution was concentrated under reduced pressure to give a semisolid residue which was triturated with acetone and filtered. Recrystallization from acetic acid/acetone gave 10.0 g. (45%) of product as colorless crystals, m.p. 178°–179°. The infra red and nmr spectra are consistent with the proposed structure.

Analysis Calcd. for $C_{10}H_{20}ClNO_2$: C, 54.20; H, 9.09; N, 6.32. Found: C, 54.21; H, 8.92; N, 6.26.

EXAMPLE 12

5(4-Homopiperidino Butyryloxy)-2,2-Dimethyl-7-[5-(4-Fluorophenyl)-2-Pentyl]-4-(4-Pyridyl)-2H-1-Benzopyran The hydroxy compound of Example 3 and the acid of Example 11 in equimolar quantities are treated with a 10% excess of dicyclohexylcarbodiimide in $CH_2Cl_2$ solvent, as described in Example 9 to give the desired product.

The present invention includes within its scope pharmaceutical compositions comprising as an active ingredient, at least one of the compounds of this invention in association with a pharmaceutically acceptable carrier or diluent. The compounds of this invention exhibit both oral and parenteral activity and can be formulated in dosage forms for oral, parenteral or rectal administration. In preparing unit dosage compositions, from 0.5 mg. to 600 mg. of active ingredient is incorporated into the appropriate form.

Solid dosage forms for oral administration include capsules, tablets, pills, powders and granules. In such solid dosage forms, the active compound is admixed with at least one inert diluent such as sucrose, lactose or starch. Such dosage forms may also comprise, as is normal practice, additional substances other than inert diluents, e.g., lubricating agents such as magnesium stearate, and sweetening and flavoring agents. Tablets and pills can additionally be prepared with enteric coatings.

Liquid dosage forms for oral administration include pharmaceutically acceptable emulsions, solutions, suspensions, syrups and elixirs containing inert diluents commonly used in the art, such as water. Besides inert diluents, such compositions can also include adjuvants, such as wetting agents, emulsifying and suspending agents and sweetening, flavoring and perfuming agents.

Preparations according to this invention for parenteral administration include sterile aqueous or nonaqueous solutions, suspensions or emulsions. Examples of nonaqueous solvents or vehicles are propylene glycol, polyethylene glycol, vegetable oils, such as olive oil, and injectable organic esters such as ethyl oleate. Such dosage forms may also contain adjuvants such as preserving, wetting, emulsifying and dispersing agents. They may be sterilized by, for example, filtration through a bacteria-retaining filter, by incorporating sterilizing agents into the compositions, by irradiating the compositions, or by heating the compositions. They can also be manufactured in the form of sterile solid compositions which can be dissolved in sterile water, or some other sterile injectable medium immediately before use.

Compositions for rectal administration are suppositories which may contain, in addition to the active substance, excipients such as cocoa butter or a suppository wax.

The following example further illustrates the pharmaceutical compositions which are a feature of this invention.

EXAMPLE 13

2-2-Dimethyl-5-Hydroxy-7-[5-(4-Fluorophenyl)-2-Pentyl]-4-(4-Pyridyl)Chroman

Tablets weighing 100 mg. and having the following composition are prepared by standard tableting procedures:

| Ingredient | Mg. |
| --- | --- |
| 2,2-Dimethyl-5-hydroxy-7-[5-(4-fluorophenyl)-2-pentyl]-4-(4-pyridyl)chroman | 50 |
| Starch | 46 |
| Colloidal silica | 3 |
| Magnesium stearate | 1 |

It will be understood by those skilled in the art that the above composition can contain any of the compounds of this invention.

We claim:

1. A compound of the formula

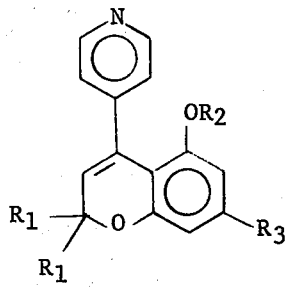

wherein each $R_1$ is loweralkyl, $R_2$ is hydrogen or loweralkanoyl and $R_3$ is

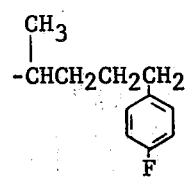

2. A compound in accordance with claim 1 wherein $R_1$ is methyl and $R_2$ is hydrogen.

3. A compound in accordance with claim 2: 2,2-dimethyl-5-hydroxy-7-[5-(4-fluorophenyl)-2-pentyl]-4-(4-pyridyl)-2H-1-benzopyran.

4. A compound in accordance with claim 1 wherein $R_1$ is methyl and $R_2$ is

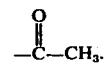

5. A compound in accordance with claim 4: 5-acetoxy-2,2-dimethyl-7-[5-(4-fluorophenyl)-2-pentyl]-4-(4-pyridyl)-2H-1-benzopyran.

* * * * *